United States Patent [19]

Wilson

[11] 4,040,931
[45] Aug. 9, 1977

[54] CORROSION RATEMETER

[75] Inventor: Homer M. Wilson, Houston, Tex.

[73] Assignee: Petrolite Corporation, St. Louis, Mo.

[21] Appl. No.: 714,559

[22] Filed: Aug. 16, 1976

[51] Int. Cl.$^2$ .................. G01N 27/46; G01N 27/26
[52] U.S. Cl. .............................................. 204/195 C
[58] Field of Search ........................ 204/1 C, 195 C

[56] References Cited

U.S. PATENT DOCUMENTS

| 3,661,750 | 5/1972 | Wilson | 204/195 C |
| 3,716,460 | 2/1973 | Weisstuch et al. | 204/1 C |
| 3,717,566 | 2/1973 | Wilson | 204/195 C |
| 3,730,869 | 5/1973 | Wilson | 204/195 C |
| 3,766,042 | 10/1973 | Wilson | 204/195 C |

Primary Examiner—John H. Mack
Assistant Examiner—Aaron Weisstuch
Attorney, Agent, or Firm—Sidney B. Ring; Hyman F. Glass

[57] ABSTRACT

An improvement to an automatic correcting type of corrosion ratemeter (e.g., U.S. Pat. No. 3,717,566) with test specimen, reference and third electrodes in contact with corrodant and "null" and "measurement" circuitry whereby correcting is made for freely corroding potential and addition of reference polarization potential between the test and reference electrodes in conjunction with controlled current flow between the test and third electrodes. The improvement comprises unique circuitry for common base, steady state readouts eliminating asynchronous cycle time problems and providing precise simultaneous readout(s) calibration.

20 Claims, 1 Drawing Figure

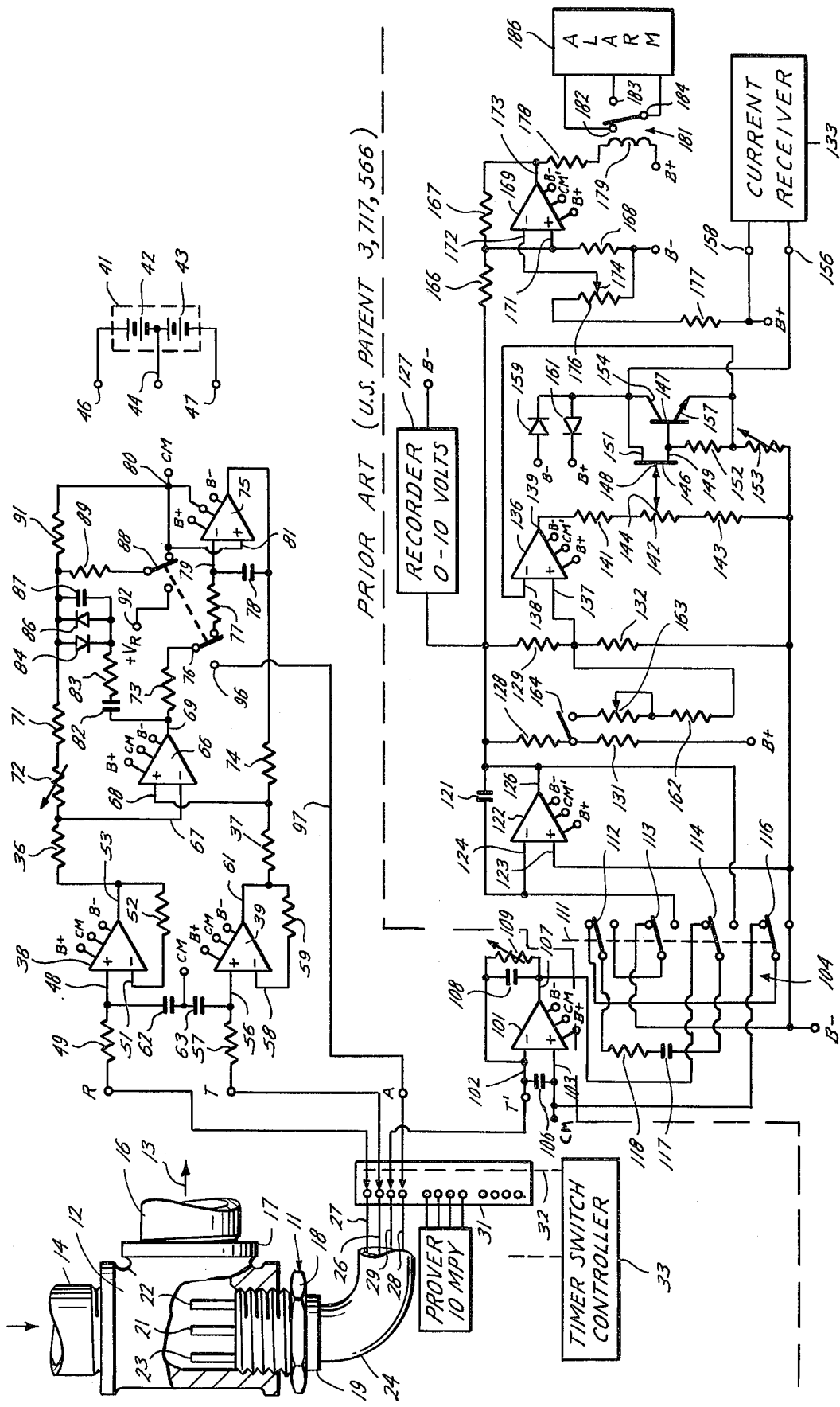

CORROSION RATEMETER

BACKGROUND OF THE INVENTION

1. Field of the Invention

This invention relates to measuring and testing corrosion processes, and it relates particularly to the instruments and electrochemical techniques used in the study of corrosion processes.

2. Description of the Prior Art

It is often desirable to determine the rates at which metals corrode within a corrodant such as a corrosive liquid. For example, corrosion inhibitors are added to aqueous liquids to reduce the corrosion of exposed metals. Instruments are used to measure the rate at which these metals corrode so that the effectiveness of the inhibitor can be determined. The measure of the rate of corrosion upon metals usually involves an instrument associated with a probe carrying electrodes immersed within the corrodant. These instruments are usually termed "corrosion ratemeters". The electrodes in the corrodant undergo certain electrochemical changes that are related to the corrosion of the specimen forming the test electrode. The rate of corrosion can be correlated with the electrochemical effects upon the test (specimen) electrode contacted by the corrodant.

An electrochemical process and apparatus, especially useful in measuring corrosion rates, is described in U.S. Pat. No. 3,406,101. In this patent, there is described a corrosion ratemeter which includes a probe having three electrodes adapted to be exposed to a corrodant such as a corrosive liquid, an adjustable current source, an ammeter and a high impedance voltmeter as primary components. The adjustable current source applies a small electric current between a "test" electrode and an "auxiliary" or third electrode. At the same time, the voltmeter monitors the polarization potential produced by current flow between the test electrode and a reference electrode. The current flow slightly polarizes the surface of the test electrode, and as a result, causes a shift in potential (polarization potential) between the test and reference electrodes. The current flow required to produce a certain desired polarization potential (usually about 10 millivolts) is directly proportional to the corrosion rate of the test electrode undergoing corrosion. Usually, the polarization is selected within the linear voltage corrosion rate environmental conditions, and good results have been obtained with between 5 and 20 millivolts, but preferably 10 millivolts, polarization.

In corrosion ratemeters of the type described in the mentioned patent, the amount of current which flows between the test and third electrodes to produce a certain polarization potential is measured to determine the rate of corrosion occurring at the test electrode. Any potential differences, such as the freely corroding potential, present between the test and reference electrodes, other than the polarizing potential, produce erroneous results in corrosion rate determinations. Obviously, these instruments can produce highly accurate results when a correction is made for the non-polarizing potential differences between electrodes, principally the freely corroding potential, which may exist between these electrodes before, and also during, applications of the polarizing current. Additionally, in these instruments correction for the freely corroding and other potentials must be made without effecting the impedance between the reference and test electrodes immersed within the corrodant. Otherwise, a constant polarizing current will produce corresponding variations in polarization potential to be developed between these electrodes.

The corrosion ratemeter can employ suitable circuitry to provide automatically an equal but opposing potential for removing the freely corroding potential from the circuit including the test and reference electrodes. The freely corroding potential is usually less than 100 millivolts and frequently is about the same magnitude as the certain polarization potential (generally 10 millivolts) to be established by controlled current between these electrodes. Thus, the input potential correcting circuitry is required to sense and then automatically remove a potential of a very small magnitude from substantially the same magnitude of the certain polarization potential to be established between these electrodes.

An automatic correcting type of corrosion ratemeter using the controlled current mode of operation is of great advantage. Circuitry is required during "null" operation to compensate for the freely corroding potential which exists as the potential difference between the reference and test electrodes in a freely corroding state when no external current flows between the electrodes. During the measurement operation of such corrosion ratemeter, the circuitry must provide a reference signal which produces a current flow between the third and test electrodes. This current must be of such a magnitude that a certain polarization potential (5-25 mv) is produced between the test and reference electrodes in addition to the freely corroding potential. Additionally, a readout means must measure the output current creating this polarization potential which current magnitude is representative of the corrosion rate occurring at the test electrode.

Various circuits have been developed for automatic correcting types of corrosion ratemeters which can perform the above functions in the proper sequence and with the necessary accuracy of measurement. Reference may be taken to U.S. Pat. Nos. 3,661,751, 3,717,566 and 3,730,869 for examples of automatic correcting types of corrosion ratemeters available in the marketplace.

In some applications, these corrosion ratemeters are required to provide simultaneous readouts in several modes, e.g., voltage recorders, remote current transmitters, digital or analog signals and alarm circuits. Presently, interface modules are usually used to convert conjunctively the current flow between the third and test electrodes into output signals suitable with the desired output. Alternatively, the interface modules may use as their inputs voltage signals from recorder outputs. As a result, each interface module requires a separate signal input base and has individual calibration requirements.

The present invention is an automatic correcting type of corrosion ratemeter wherein the basic null and measurement circuitry can be of suitable design as in the above mentioned patents. As an improvement to these corrosion ratemeters, this invention provides a unique circuitry wherein all readouts have a common base for all signals. These signals hve the same relationship to one another throughout the dynamic range of these corrosion ratemeters. As a result, calibration of these corrosion ratemeters for any one readout simultaneously produces the precise calibration of all other readouts. In addition, the readouts are steady state values during both null and measurement operations as contrasted with the more conventional asynchronous readouts that complicate both analog and digital data processing on varying readouts.

SUMMARY OF THE INVENTION

In accordance with this invention, there is provided an improvement to a corrosion ratemeter having reference, test and third electrodes adapted to be placed into contact with a corrodant; a voltage loop circuit including a voltage comparator between the reference and test electrodes; a current loop circuit including a current source means between the test and third electrodes; and a signal correction means and reference signal means associated with said voltage and current loops for freely corroding potential correction and addition of reference polarization potential. In this type of corrosion ratemeter, a current-to-voltage converting means in the current loop provides a voltage signal proportional to current flow in the current loop; the improvement comprises (a) first capacitance means connected to the current-to-voltage converting means for storing a first voltage proportional in magnitude to the voltage signal, (b) storage means having a second capacitance means with a second voltage therein; (c) switch means for periodically connecting the first capacitance means across the storage means whereby the second capacitance means stores a resultant voltage, which resultant voltage is in proportion to the first voltage by the capacitance ratio of the first capacitance means to the sum of the first and second capacitance means, and summed with the second voltage on the second capacitance means by the capacitance ratio of the second capacitance means to the sum of the first and second capacitance means; and (d) readout means receiving the resultant voltage to provide an output indicative thereof.

BRIEF DESCRIPTION OF THE DRAWING

The FIGURE in the drawing includes a prospective view above a chain line of prior art automatic correcting type of corrosion ratemeter, probe and piping system, and an illustrative embodiment of the present improvement thereto in unique circuitry beneath the chain line.

DESCRIPTION OF SPECIFIC EMBODIMENTS

In the drawing, an automatic correcting type of corrosion ratemeter, probe and piping system in the prior art is shown above the chain line. This illustration is identical to the basic null and measurement circuitry of the instrument described in U.S. Pat. No. 3,717,566. For simplicity, like elements bear like numeral references in the drawing as they appear in this patent to which reference may be taken for a detailed description of the corrosion ratemeter.

Generally, the prior art arrangement includes a probe 11 carrying metal electrodes 21, 22 and 23 in contact with a corrodant. The electrodes connect by conductors 26 through 29 to terminals (R, T, T', A) on the corrosion ratemeter. Reference and test electrodes connect to terminals R and T in a voltage loop including voltage amplifiers 38 and 39 which form a voltage comparator with amplifier 66. The amplifier 75 provides for balancing the electrical bridge including these amplifiers with respect to freely corroding potential at the reference electrode 21 and test electrode 22 during null operation with the switch 76 in the indicated position. The amplifier 66 is a current source in a current loop including test electrode 22 and third electrode 23. In measurement operation, a source of reference signal voltage $\pm V_R$ is applied to the electrical flow between electrodes 22 and 23 whereby a certain d.c. potential (e.g., 10 mv.) is induced as a polarization potential between reference electrode 21 and test electrode 22. The switching between null and measurement operation for proper functioning of the corrosion ratemeter can be provided by the controller 33.

The current loop circuit from the test electrode 21 is completed by conductor 29 to terminal T' and circuit common (CM) 80. In prior art instruments, various interface modules sensed the current flow in the conductor 29 and provided output signals individually tailored to each readout device to be utilized, e.g., analog or digital, voltage driven recorders, current transmitter-receiver combinations, alarms circuits, etc. As a result, each interface module requires a separate input base and has individual calibration problems. Also, the readouts were not steady state and reflected asynchronous time cycles in the null and measurement operations of the corrosion ratemeter, especially in the automatic correction types.

Amplifier 101 is arranged to provide a current-to-voltage converter and has input 102 connected to terminal T' and input 103 connected to a multipole, dual-throw contactor 104. The inputs 102 and 103 are bypassed for transient voltages by a capacitor 106. The amplifier 101 has an output 107 also connected to contactor 104 with a feedback circuit including paralleled capacitor 108 and variable resistor 109 to the input 102 for gain control function.

This arrangement of the amplifier 101 produces a d.c. voltage signal at the output 107 that is proportional in fixed ratio to the current flow magnitude in the current loop from the conductor 29 to circuit common. The ratio of proportionality can be adjusted with the resistor 109 which serves as a range selector.

In the present improvement, the current flow in the conductor 29 between terminal T' and circuit common producing the voltage signal at output 107 is monitored by the following unique circuitry beneath the chain line.

The contactor 104 as indicated by chain line 111 is activated by controller 33 and is shown in the "sample" operating position. The other operating position of contactor 104 is the "hold" position. In any event, the contactor 104 is always in the hold position when the corrosion ratemeter is in null operation. Only during the last portion of the measurement operation of the corrosion ratemeter is the contactor 104 in the sample position. The contactor 104 has sections 112, 113, 114 and 116 that represent DPDT switching function. A capacitor 117 with series resistor 118 connects to sections 112, and 114 to provide a memory function in sample position. In sample operation, the voltage signal at the output 107 will be applied to capacitor 117 in a time function represented by the RC time constant of capacitor 117 and resistor 118 so as to avoid any spurious voltages being generated at the output 107. The capacitor 117 now has stored a first voltage that is directly proportional to the voltage signal at the output 107 of amplifier 101 during sample operating position of contactor 104.

The contactor 104 is actuated by controller 33 into the hold position at the end of the measurement operation and during all of the null operation of the corrosion ratemeter. During hold, the capacitor 117 is switched, into a signal holding memory, across a capacitor 121 of an amplifier 122.

More particularly, the amplifier 122 has an input 123 connected to section 116 and an input 124 connected to section 113 of the contactor 104. The capacitor 121 is the feedback circuit between input 124 and output 126 of amplifier 122. The output 126 also is connected to section 114 of the contactor. This arrangement places the capacitor 117 in parallel with capacitor 121 of amplifier 122 during the hold operation. The capacitor 121 receives and stores a voltage in direct proportion to the voltage stored in the "flying" capacitor 117. This stored voltage is determined by initial voltage in the capacitor 121 and the capacitance ratio of capacitor 117 to capacitance 117 plus 121. Preferably, the capacitor 17 is at least 100 times the capacitance of capacitor 121 so that the voltages stored in the capacitor 121 represents 99 percent of the total voltage magnitude. As a result, once the capacitor 121 stores the voltage, the capacitor 117 can be removed and the capacitor 121 holds 99 percent of the voltage assuming perfect operational amplifier 122.

The test electrode of the probe 11 (terminals T' and CM) is isolated from terminal CM' of amplifiers 122, 136, and 169 by the circuitry of the readout means of the present invention. These amplifiers are supplied the usual B+, B− and CM' from a separate floating power supply not in common with the prior art circuitry. Thus, the capacitors 117 and 121 store voltages representing current flow in the current loop and the readout circuitry is isolated from the prior art measurement circuitry. the capacitor 121 stores a voltage that is the voltage resultant when the charge in capacitor 117 is impressed in shunt with the charge in capacitor 12.

More particularly, the charges in the capacitor 121 in sample and hold are substantially the same in magnitude at steady state operation. Therefore, at hold operation, the voltage stored in capacitor 121 time the product of capacitances in capacitors 117 and 121 is equal, for practical purposes, at sample operation to the voltage stored in capacitor 121 times the capacitance of capacitor 121 added to the voltage stored in capacitor 117 times the capacitance of capacitor 117. When the voltage stored in capacitor 117 reaches a steady state value, the voltage stored in capacitor 121 approaches exactly the same magnitude. However, a change in the voltage stored in the capacitor 117 results in the capacitor 121 approaching the same magnitude but differing therefrom only as to each individual change in voltage times the ratio of the capacitances of capacitor 117 to capacitor 121. For example, if capacitor 117 is 100 times the capacitance of capacitor 121, a change in voltage stored at hold operation in capacitor 121 is 99 percent of the change in voltage stored in capacitor 117 at sample operation.

During all operation of the corrosion ratemeter, the capacitor 121 stores the voltage representing current flow in the current loop that existed during the sample operation in the last portion of the measurement operation. The amplifier 122 maintains this stored voltage at its output 126. Any readout device, such as a voltage driven recorder 127, can be connected between the output 126 and circuit common to produce a readout corresponding to the voltage in the capacitor 121.

Preferably, a high impedance network is connected to the input 137 of amplifier 136 to provide current transmitter output proportional to the voltage in the capacitor 121. In the improvement shown in the drawing, the network is formed by a four arm impedance balanced, electrical bridge. The bridge is formed of like resistors 128 and 129 and like resistors 131 and 132. The junction of the resistor 128 and 129 connects to output 126, and the opposite junction of resistors 131 and 132 connects to d.c. power source B+ and circuit common or B−. The bridge always reflects in its arms 129 and 132 a voltage proportional to the voltage stored in capacitor 121. The voltage output of the arms 128 and 131 of the bridge is always directly proportional to the voltage stored in capacitor 121 plus the stable B+ voltage. The amplifier 122 provides steady state voltage conditions for all readout devices including the bridge arrangement.

A current receiver 133 as a readout device can be used. In this arrangement, an amplifier 136 connects across the resistor 132 with inputs 137 and 138 to receive a voltage signal selected in a desired proportion to the voltage held in capacitor 121 plus a fixed voltage signal in proportion to B+ as set by selection of resistor 163 and resistor 162 when switch 164 is closed. The output 139 provides a voltage signal across load network resistors 141, 142 and 143 connected to circuit common. The resistor 142 has a variable tap 144 which permits current limiting adjustment to current receiver 133.

The amplifier 146 may be a FET type with a gate 148 connected to a voltage source 144 and a drain 149 connected through resistors 152 and 153 to circuit common. The resistor 153 is variable and is used to set the proportionality of current output from the amplifier 147, to current receiver 133 with respect to the voltage on capacitor 121. The source 151 of amplifier 146 connects with a collector 154 of amplifier 147 and the current transmitter output terminal 156 to the current receiver 133. The emitter 157 connects in shunt to resistor 152 and input 138 of amplifier 136. A second terminal 158 of the current receiver 133 connects to d.c. source B+. Diodes 159 and 161 across the d.c. source provide circuit protection for the amplifiers 146 and 147 in case of misapplication of external voltage sources at the current receiver terminals 156 and 158.

The resistor 153 is selected so that the current flow to the collector 154 of amplifier 147 is in the desired proportion to the voltage magnitude held in capacitor 121 of the amplifier 122.

In some instances, the current transmitter is required to have a "non-zero" readout of a fixed percentage of full scale current (e.g., 20 percent of maximum current flow) when the voltage on capacitor 121 is zero. By using the high impedance balanced electrical bridge in the output of amplifier 122, the current offset is readily provided. For this purpose, shunt resistors 162 and 163 are selectively connected across the bridge by switch 164. Resistor 163 can be variable and the total shunt resistance is such that closing the switch 164 produces the corresponding shift in voltage across resistor 132 to the input 137 of amplifier 136.

An alarm circuit can be operated from the voltage at the output of 122. For example, the voltage from output 122 is "divided" down across voltage divider resistors 166 and 168 to circuit common or B−. A current amplifier 169 has an input 171 connected between resistors 166 and 168 with the resistor 167 forming the feedback from output 173 to input 171, thus providing hysteresis about the "set point" of the alarm function. The second input 172 of amplifier 169 receives a reference set point voltage from a tap 174 on resistor 176 which connects between circuit common and a d.c. source B+ through divider resistor 177. The output 173 connects to the d.c.

source B+ through a limiting resistor 178 and coil 179 of relay 181. The relay 181 is actuated whenever the voltage in input 171 is equal to, or greater than, the set point voltage on input 172. The relay has contacts 182, 183 and 184 connected to terminals of a remote alarm device 186 which may be a bell, light, etc. Obviously, the input voltage at input 171 to the amplifier 169 is always a certain proportion of the voltage in the capacitor 121 (and the bridge). Therefore, as with the recorder 127 and current transmitter, all readout devices operate directly from the same source, i.e., the voltage stored in capacitor 121. Therefore, adjustment of the corrosion ratemeter circuitry for calibration resistor 109 simultaneously corrects all readout devices by the same ratio.

In an example of the functioning of the present improvement in circuitry, the contactor 104 is operated from the controller 33 in the following manner. The switches 76 and 88 of the corrosion ratemeter are placed in null and measurement operation position for equal time periods, e.g. 30 seconds. During the last portion of measurement operation, the contactor 104 places the flying capacitor 117 in the output of current-to-voltage amplifier 101 to receive and store the voltage signal proportional to current flow in the current loop. The function may be termed the sample position of the contactor 104 and is of short time duration, e.g., 10 seconds. During the remainder of the null and measurement operation of the corrosion ratemeter, the contactor 104 remains in the hold position whereby the capacitor 117 is in parallel with the capacitor 121 of the amplifier 122. The readout devices will have a steady state value all during the hold position of contactor 104. This feature eliminates the constant variation of the readouts during operation of the usual corrosion ratemeter and simplifies the problems associated with asynchronous time cycles and conversion to analog or digital readout signals.

The amplifier 101, and the other amplifiers heretofore discussed, have the usual connections to the d.c. power source B+ and B− and circuit common.

Although the present improvement in circuitry can be used to great advantage with automatic correction types of corrosion ratemeters, it has special utility with manually operated instruments such as shown in U.S. Pat. Nos. 3,406,101, 3,616,417 and 3,766,042.

Various changes and alterations will be apparent to those skilled in the art of the circuitry of the corrosion ratemeter of the present invention. It is intended that such changes and alterations, which do not depart from the spirit of the present invention, be included within the scope of the appended claims. The appended claims define the present invention; the foregoing description is employed for setting forth the present invention embodiments as illustrative in nature.

What is claimed is:

1. In a corrosion ratemeter having reference, test and third electrodes adapted to be placed into contact with a corrodant, a voltage loop circuit including a voltage comparator connecting said reference and test electrodes, a current loop circuit including a current source means connecting said test and third electrodes, signal correction means and reference signal means associated with said voltage and current loops for freely corroding potential correction and polarization potential addition therein and current-to-voltage converting means in said current loop provide a voltage signal proportional to current flow in said current loop; the improvement comprising:

a. first capacitance means connected with said current-to-voltage converting means for storing a first voltage proportional in magnitude to said voltage signal;
b. storage means having a second capacitance with means with a second voltage therein; and
c. means for periodically connecting the first capacitance means across the storage means whereby the second capacitance means stores a resultant voltage, which resultant voltage is in proportion to the first voltage by the capacitance ratio of the first capacitance means to the sum of the first and second capacitance means, and summed with the second voltage on the second capacitance means by the capacitance ratio of the second capacitance means to the sum of the first and second capacitance means.

2. The corrosion ratemeter of claim 1 further including readout means receiving said resultant voltage to provide an output indicative thereof.

3. The corrosion ratemeter of claim 2 wherein said readout means includes recorders, alarm circuitry and current transmitter means.

4. The corrosion ratemeter of claim 3 wherein said means for periodically connecting the first capacitance means across the storage means is switch means.

5. The corrosion ratemeter of claim 2 wherein said storage means has an output connected at one corner of four arm impedance balanced electrical bridge with the opposite corner thereof at circuit common relative to a source of d.c. potential connected into the bridge, and the bridge output to said readout means is taken across an arm of said bridge whereby said bridge output is proportional to the sum of the output of the storage means and the source of d.c. potential.

6. The corrosion ratemeter of claim 5 wherein said means for periodically connecting the first capacitance means across the storage means is switch means.

7. The corrosion ratemeter of claim 2 wherein said readout means is a current transmitter means receiving said resultant voltage, said current transmitter means comprising an amplifier receiving said resultant voltage as an input and providing an output signal to a current amplifier means having an output current signal proportional to said resultant voltage.

8. The corrosion ratemeter of claim 7 wherein said current transmitter means receives said resultant voltage biased by an offset voltage from a voltage source means whereby said output current signal is offset from zero magnitude of said resultant voltage by a certain percentage of the maximum magnitude of said output current signal.

9. The corrosion ratemeter of claim 8 wherein said means for periodically connecting the first capacitance means across the storage means is switch means.

10. The corrosion ratemeter of claim 7 wherein said current amplifier means includes voltage to current proportioning means whereby said output current signal can be adjusted independently in proportion to said resultant voltage signal.

11. The corrosion ratemeter of claim 10 wherein said current amplifier means is a power transistor being base driven from said amplifier through a field effect transistor having selectable gate biasing for limiting the magnitude of said output signal from said power transistor.

12. The corrosion ratemeter of claim 11 wherein said means for periodically connecting the first capacitance means across the storage means is switch means.

13. The corrosion ratemeter of claim 10 wherein said means for periodically connecting the first capacitance means across the storage means is switch means.

14. The corrosion ratemeter of claim 7 wherein said means for periodically connecting the first capacitance means across the storage means is switch means.

15. The corrosion ratemeter of claim 2 wherein said readout means includes an alarm circuit means receiving said resultant voltage as one input with a second input at a set point voltage signal and having an output circuit including contactor means adapted to complete one or more alarm signal circuits.

16. The corrosion ratemeter of claim 15 wherein said means for periodically connecting the first capacitance means across the storage means is switch means.

17. The corrosion ratemeter of claim 1 wherein said storage means has an output connected at one corner of four arm impedance balanced electrical bridge with the opposite corner thereof at circuit common relative to a source of d.c. potential connected into the bridge.

18. The corrosion ratemeter of claim 17 wherein said means for periodically connecting the first capacitance means across the storage means is switch means.

19. The corrosion ratemeter of claim 2 wherein said means for periodically connecting the first capacitance means across the storage means is switch means.

20. The corrosion ratemeter of claim 1 wherein said means for periodically connecting the first capacitance means across the storage means is switch means.

* * * * *